US008668129B2

(12) United States Patent
Olson (10) Patent No.: US 8,668,129 B2
(45) Date of Patent: Mar. 11, 2014

(54) SURGICAL APPARATUS INCLUDING SURGICAL BUTTRESS

(75) Inventor: Lee Olson, Wallingford, CT (US)

(73) Assignee: Covidien LP, Mansfield, MA (US)

( * ) Notice: Subject to any disclaimer, the term of this patent is extended or adjusted under 35 U.S.C. 154(b) by 0 days.

(21) Appl. No.: 13/151,340

(22) Filed: Jun. 2, 2011

(65) Prior Publication Data

US 2011/0233259 A1 Sep. 29, 2011

Related U.S. Application Data

(63) Continuation of application No. 12/620,044, filed on Nov. 17, 2009, which is a continuation of application No. 12/335,762, filed on Dec. 16, 2008.

(51) Int. Cl.
*A61B 17/064* (2006.01)
(52) U.S. Cl.
USPC .......................................... 227/175.1; 227/19
(58) Field of Classification Search
USPC ................... 227/175.1–182.1, 19; 606/219
See application file for complete search history.

(56) References Cited

U.S. PATENT DOCUMENTS

| | | | |
|---|---|---|---|
| 3,054,406 A | 9/1962 | Usher | |
| 3,124,136 A | 3/1964 | Usher | |
| 4,347,847 A | 9/1982 | Usher | |
| 4,354,628 A | 10/1982 | Green | |
| 4,452,245 A | 6/1984 | Usher | |
| 4,605,730 A | 8/1986 | Shalaby et al. | |
| 4,655,221 A | 4/1987 | Devereux | |
| 4,834,090 A | 5/1989 | Moore | |
| 4,838,884 A | 6/1989 | Dumican et al. | |
| 4,927,640 A | 5/1990 | Dahlinder et al. | |
| 4,930,674 A | 6/1990 | Barak | |
| 5,002,551 A | 3/1991 | Linsky et al. | |
| 5,014,899 A | 5/1991 | Presty et al. | |
| 5,040,715 A | 8/1991 | Green et al. | |

(Continued)

FOREIGN PATENT DOCUMENTS

DE 1 99 24 311 A1 11/2000
DE 199 24 311 A1 11/2000

(Continued)

OTHER PUBLICATIONS

International Search Report corresponding to European Application No. EP 06 00 4598, completed on Jun. 22, 2006; 2 pages.

(Continued)

*Primary Examiner* — Brian D Nash (57) ABSTRACT

A surgical buttress includes a body portion and a band disposed on each of the distal and proximal ends thereof. The surgical buttress is configured to attach to an end effector of a surgical stapling apparatus. The body portion, having perforations disposed thereon, overlies the working surface of one of the first or second jaws of the end effector. A resilient portion extends transversely beyond the side edges of the first or second jaws. Each band remains attached to the end effector following the firing thereof. The proximal band is removably attachable to a hook feature disposed on one of the first or second jaws of the end effector. The surgical buttress can be made from suitable degradable or non-degradable materials. One embodiment contemplates a detachable and disposable single use loading unit. A method of attaching the surgical buttress to a surgical apparatus is also envisioned.

16 Claims, 5 Drawing Sheets (56) References Cited

U.S. PATENT DOCUMENTS

| | | |
|---|---|---|
| 5,065,929 A | 11/1991 | Schulze et al. |
| 5,205,459 A | 4/1993 | Brinkerhoff et al. |
| 5,263,629 A | 11/1993 | Trumbull et al. |
| 5,314,471 A | 5/1994 | Brauker et al. |
| 5,344,454 A | 9/1994 | Clarke et al. |
| 5,392,979 A | 2/1995 | Green et al. |
| 5,397,324 A | 3/1995 | Carroll et al. |
| 5,425,745 A | 6/1995 | Green et al. |
| 5,441,193 A | 8/1995 | Gravener |
| 5,441,507 A | 8/1995 | Wilk et al. |
| 5,443,198 A | 8/1995 | Viola et al. |
| 5,468,253 A | 11/1995 | Bezwada et al. |
| 5,503,638 A | 4/1996 | Cooper et al. |
| 5,542,594 A | 8/1996 | McKean et al. |
| 5,549,628 A | 8/1996 | Cooper et al. |
| 5,575,803 A | 11/1996 | Cooper et al. |
| 5,653,756 A | 8/1997 | Clarke et al. |
| 5,683,809 A | 11/1997 | Freeman et al. |
| 5,690,675 A | 11/1997 | Sawyer et al. |
| 5,702,409 A | 12/1997 | Rayburn et al. |
| 5,752,965 A | 5/1998 | Francis et al. |
| 5,762,256 A | 6/1998 | Mastri et al. |
| 5,766,188 A | 6/1998 | Igaki |
| 5,769,892 A | 6/1998 | Kingwell |
| 5,782,396 A | 7/1998 | Mastri et al. |
| 5,799,857 A | 9/1998 | Robertson et al. |
| 5,810,855 A | 9/1998 | Rayburn et al. |
| 5,814,057 A | 9/1998 | Oi et al. |
| 5,833,695 A | 11/1998 | Yoon |
| 5,843,096 A | 12/1998 | Igaki et al. |
| 5,895,412 A | 4/1999 | Tucker |
| 5,895,415 A | 4/1999 | Chow et al. |
| 5,902,312 A | 5/1999 | Frater et al. |
| 5,908,427 A | 6/1999 | McKean et al. |
| 5,915,616 A | 6/1999 | Viola et al. |
| 5,931,847 A | 8/1999 | Bittner et al. |
| 5,964,774 A | 10/1999 | McKean et al. |
| 5,997,895 A | 12/1999 | Narotam et al. |
| 6,019,791 A | 2/2000 | Wood |
| 6,030,392 A | 2/2000 | Dakov et al. |
| 6,032,849 A | 3/2000 | Mastri et al. |
| 6,045,560 A | 4/2000 | McKean et al. |
| 6,063,097 A | 5/2000 | Oi et al. |
| 6,080,169 A | 6/2000 | Turtel |
| 6,099,551 A | 8/2000 | Gabbay |
| 6,149,667 A | 11/2000 | Hovland et al. |
| 6,155,265 A | 12/2000 | Hammerslag |
| 6,210,439 B1 | 4/2001 | Firmin et al. |
| 6,214,020 B1 | 4/2001 | Mulhauser et al. |
| 6,241,139 B1 | 6/2001 | Milliman et al. |
| 6,258,107 B1 | 7/2001 | Balazs et al. |
| 6,267,772 B1 | 7/2001 | Mulhauser et al. |
| 6,273,897 B1 | 8/2001 | Dalessandro et al. |
| 6,280,453 B1 | 8/2001 | Kugel et al. |
| 6,299,631 B1 | 10/2001 | Shalaby |
| 6,312,457 B1 | 11/2001 | DiMatteo et al. |
| 6,312,474 B1 | 11/2001 | Francis et al. |
| 6,325,810 B1 | 12/2001 | Hamilton et al. |
| 6,436,030 B2 | 8/2002 | Rehil |
| 6,454,780 B1 | 9/2002 | Wallace |
| 6,461,368 B2 | 10/2002 | Fogarty et al. |
| 6,503,257 B2 | 1/2003 | Grant et al. |
| 6,514,283 B2 | 2/2003 | DiMatteo et al. |
| 6,517,566 B1 | 2/2003 | Hovland et al. |
| 6,551,356 B2 | 4/2003 | Rousseau |
| 6,592,597 B2 | 7/2003 | Grant et al. |
| 6,638,285 B2 | 10/2003 | Gabbay |
| 6,652,594 B2 | 11/2003 | Francis et al. |
| 6,656,193 B2 | 12/2003 | Grant et al. |
| 6,669,735 B1 | 12/2003 | Pelissier |
| 6,677,258 B2 | 1/2004 | Carroll et al. |
| 6,685,714 B2 | 2/2004 | Rousseau |
| 6,704,210 B1 | 3/2004 | Myers |
| 6,723,114 B2 | 4/2004 | Shalaby |
| 6,726,706 B2 | 4/2004 | Dominguez |
| 6,736,823 B2 | 5/2004 | Darois et al. |
| 6,736,854 B2 | 5/2004 | Vadurro et al. |
| 6,746,458 B1 | 6/2004 | Cloud |
| 6,773,458 B1 | 8/2004 | Brauker et al. |
| 6,927,315 B1 | 8/2005 | Heinecke et al. |
| 7,128,748 B2 | 10/2006 | Mooradian et al. |
| 7,147,138 B2 | 12/2006 | Shelton, IV |
| 7,434,717 B2 | 10/2008 | Shelton, IV et al. |
| 7,438,209 B1 | 10/2008 | Hess et al. |
| 7,547,312 B2 | 6/2009 | Bauman et al. |
| 7,559,937 B2 | 7/2009 | de la Torre et al. |
| 7,604,151 B2 | 10/2009 | Hess et al. |
| 7,665,646 B2 | 2/2010 | Prommersberger |
| 7,669,747 B2 | 3/2010 | Weisenburgh, II et al. |
| 7,717,313 B2 | 5/2010 | Criscuolo et al. |
| 7,744,627 B2 | 6/2010 | Orban, III et al. |
| 7,793,813 B2 | 9/2010 | Bettuchi |
| 7,799,026 B2 | 9/2010 | Schechter et al. |
| 7,823,592 B2 | 11/2010 | Bettuchi et al. |
| 7,845,533 B2 | 12/2010 | Marczyk et al. |
| 7,845,536 B2 | 12/2010 | Viola et al. |
| 7,909,224 B2 | 3/2011 | Prommersberger |
| 8,225,799 B2 | 7/2012 | Bettuchi |
| 8,225,981 B2 | 7/2012 | Criscuolo et al. |
| 8,308,045 B2 | 11/2012 | Bettuchi et al. |
| 8,312,885 B2 | 11/2012 | Bettuchi et al. |
| 8,365,972 B2 | 2/2013 | Aranyi et al. |
| 8,424,742 B2 | 4/2013 | Bettuchi |
| 8,464,925 B2 | 6/2013 | Hull et al. |
| 8,485,414 B2 | 7/2013 | Criscuolo et al. |
| 2002/0016626 A1 | 2/2002 | DiMatteo et al. |
| 2002/0019187 A1 | 2/2002 | Carroll et al. |
| 2002/0028243 A1 | 3/2002 | Masters |
| 2002/0052622 A1 | 5/2002 | Rousseau |
| 2002/0091397 A1 | 7/2002 | Chen |
| 2002/0133236 A1 | 9/2002 | Rousseau |
| 2002/0138152 A1 | 9/2002 | Francis et al. |
| 2002/0151911 A1 | 10/2002 | Gabbay |
| 2002/0165559 A1 | 11/2002 | Grant et al. |
| 2002/0165562 A1 | 11/2002 | Grant et al. |
| 2002/0165563 A1 | 11/2002 | Grant et al. |
| 2002/0177859 A1 | 11/2002 | Monassevitch et al. |
| 2003/0065345 A1 | 4/2003 | Weadock |
| 2003/0065346 A1 | 4/2003 | Evens et al. |
| 2003/0083676 A1 | 5/2003 | Wallace |
| 2003/0088256 A1 | 5/2003 | Conston et al. |
| 2003/0105510 A1 | 6/2003 | DiMatteo et al. |
| 2003/0114866 A1 | 6/2003 | Ulmsten et al. |
| 2003/0120284 A1 | 6/2003 | Palacios |
| 2003/0167064 A1 | 9/2003 | Whayne |
| 2003/0181927 A1 | 9/2003 | Wallace |
| 2003/0183671 A1 | 10/2003 | Mooradian et al. |
| 2003/0208231 A1 | 11/2003 | Williamson, IV et al. |
| 2004/0034377 A1 | 2/2004 | Sharkawy et al. |
| 2004/0092960 A1 | 5/2004 | Abrams et al. |
| 2004/0093029 A1 | 5/2004 | Zubik et al. |
| 2004/0107006 A1 | 6/2004 | Francis et al. |
| 2004/0116945 A1 | 6/2004 | Sharkawy et al. |
| 2004/0142621 A1 | 7/2004 | Carroll et al. |
| 2004/0172048 A1 | 9/2004 | Browning |
| 2004/0209059 A1 | 10/2004 | Foss |
| 2004/0215214 A1 | 10/2004 | Crews et al. |
| 2004/0215219 A1 | 10/2004 | Eldridge et al. |
| 2004/0215221 A1 | 10/2004 | Suyker et al. |
| 2004/0254590 A1 | 12/2004 | Hoffman et al. |
| 2004/0260315 A1 | 12/2004 | Dell et al. |
| 2005/0002981 A1 | 1/2005 | Lahtinen et al. |
| 2005/0021026 A1 | 1/2005 | Baily |
| 2005/0021053 A1 | 1/2005 | Heinrich |
| 2005/0021085 A1 | 1/2005 | Abrams et al. |
| 2005/0059996 A1 | 3/2005 | Bauman et al. |
| 2005/0059997 A1 | 3/2005 | Bauman et al. |
| 2005/0070929 A1 | 3/2005 | Dalessandro et al. |
| 2005/0118435 A1 | 6/2005 | DeLucia et al. |
| 2005/0143756 A1 | 6/2005 | Jankowski |
| 2005/0149073 A1 | 7/2005 | Arani et al. |
| 2005/0228446 A1 | 10/2005 | Mooradian et al. |
| 2005/0245965 A1 | 11/2005 | Orban et al. |
| 2006/0004407 A1 | 1/2006 | Hiles et al. |

(56) References Cited

U.S. PATENT DOCUMENTS

| | | |
|---|---|---|
| 2006/0085034 A1 | 4/2006 | Bettuchi |
| 2006/0135992 A1 | 6/2006 | Bettuchi |
| 2006/0173470 A1 | 8/2006 | Oray et al. |
| 2006/0178683 A1 | 8/2006 | Shimoji et al. |
| 2006/0212050 A1 | 9/2006 | D'Agostino et al. |
| 2006/0271104 A1 | 11/2006 | Viola et al. |
| 2007/0026031 A1 | 2/2007 | Bauman et al. |
| 2007/0027472 A1* | 2/2007 | Hiles et al. ................ 606/215 |
| 2007/0034669 A1 | 2/2007 | de la Torre et al. |
| 2007/0049953 A2 | 3/2007 | Shimoji et al. |
| 2007/0123839 A1 | 5/2007 | Rousseau et al. |
| 2007/0179528 A1 | 8/2007 | Soltz et al. |
| 2007/0203509 A1 | 8/2007 | Bettuchi |
| 2007/0203510 A1 | 8/2007 | Bettuchi |
| 2007/0246505 A1 | 10/2007 | Pace-Floridia et al. |
| 2008/0029570 A1 | 2/2008 | Shelton et al. |
| 2008/0082126 A1 | 4/2008 | Murray et al. |
| 2008/0110959 A1 | 5/2008 | Orban et al. |
| 2008/0125812 A1 | 5/2008 | Zubik et al. |
| 2008/0140115 A1 | 6/2008 | Stopek |
| 2008/0161831 A1 | 7/2008 | Bauman et al. |
| 2008/0161832 A1 | 7/2008 | Bauman et al. |
| 2008/0169327 A1 | 7/2008 | Shelton et al. |
| 2008/0169328 A1 | 7/2008 | Shelton |
| 2008/0169329 A1 | 7/2008 | Shelton et al. |
| 2008/0169330 A1 | 7/2008 | Shelton et al. |
| 2008/0169331 A1 | 7/2008 | Shelton et al. |
| 2008/0169332 A1 | 7/2008 | Shelton et al. |
| 2008/0169333 A1 | 7/2008 | Shelton et al. |
| 2008/0290134 A1 | 11/2008 | Bettuchi et al. |
| 2008/0308608 A1 | 12/2008 | Prommersberger |
| 2008/0314960 A1 | 12/2008 | Marczyk et al. |
| 2009/0001121 A1 | 1/2009 | Hess et al. |
| 2009/0001122 A1 | 1/2009 | Prommersberger et al. |
| 2009/0001123 A1 | 1/2009 | Morgan et al. |
| 2009/0001124 A1 | 1/2009 | Hess et al. |
| 2009/0001125 A1 | 1/2009 | Hess et al. |
| 2009/0001126 A1 | 1/2009 | Hess et al. |
| 2009/0001128 A1 | 1/2009 | Weisenburgh, II et al. |
| 2009/0001130 A1 | 1/2009 | Hess et al. |
| 2009/0005808 A1 | 1/2009 | Hess et al. |
| 2009/0030452 A1 | 1/2009 | Bauman et al. |
| 2009/0043334 A1 | 2/2009 | Bauman et al. |
| 2009/0076510 A1 | 3/2009 | Bell et al. |
| 2009/0076528 A1 | 3/2009 | Sgro |
| 2009/0078739 A1 | 3/2009 | Viola |
| 2009/0095791 A1 | 4/2009 | Eskaros et al. |
| 2009/0095792 A1 | 4/2009 | Bettuchi |
| 2009/0120994 A1 | 5/2009 | Murray et al. |
| 2009/0134200 A1 | 5/2009 | Tarinelli et al. |
| 2009/0206125 A1 | 8/2009 | Huitema et al. |
| 2009/0206126 A1 | 8/2009 | Huitema et al. |
| 2009/0206139 A1 | 8/2009 | Hall et al. |
| 2009/0206141 A1 | 8/2009 | Huitema et al. |
| 2009/0206142 A1 | 8/2009 | Huitema et al. |
| 2009/0206143 A1 | 8/2009 | Huitema et al. |
| 2009/0218384 A1 | 9/2009 | Aranyi |
| 2009/0277947 A1 | 11/2009 | Viola |
| 2009/0287230 A1 | 11/2009 | D'Agostino et al. |
| 2010/0012704 A1 | 1/2010 | Tarinelli Racenet et al. |
| 2010/0065606 A1 | 3/2010 | Stopek |
| 2010/0065607 A1 | 3/2010 | Orban, III et al. |
| 2010/0072254 A1 | 3/2010 | Aranyi et al. |
| 2010/0147921 A1 | 6/2010 | Olson |
| 2010/0147922 A1 | 6/2010 | Olson |
| 2010/0147923 A1 | 6/2010 | D'Agostino et al. |
| 2010/0243708 A1 | 9/2010 | Aranyi et al. |
| 2010/0243711 A1 | 9/2010 | Olson et al. |
| 2010/0249622 A1 | 9/2010 | Olson |
| 2010/0249805 A1 | 9/2010 | Olson et al. |
| 2010/0264195 A1 | 10/2010 | Bettuchi |
| 2010/0282815 A1 | 11/2010 | Bettuchi et al. |
| 2011/0024476 A1 | 2/2011 | Bettuchi et al. |
| 2011/0024481 A1 | 2/2011 | Bettuchi et al. |
| 2011/0036894 A1 | 2/2011 | Bettuchi |
| 2011/0042442 A1 | 2/2011 | Viola et al. |
| 2011/0046650 A1 | 2/2011 | Bettuchi |
| 2011/0057016 A1 | 3/2011 | Bettuchi |
| 2011/0087279 A1 | 4/2011 | Shah et al. |
| 2012/0273547 A1 | 11/2012 | Hodgkinson et al. |
| 2013/0037596 A1 | 2/2013 | Bear et al. |

FOREIGN PATENT DOCUMENTS

| | | |
|---|---|---|
| EP | 0 594 148 A1 | 4/1994 |
| EP | 0 327 022 B1 | 4/1995 |
| EP | 0 667 119 A1 | 8/1995 |
| EP | 1 064 883 A1 | 1/2001 |
| EP | 1 256 317 A2 | 11/2002 |
| EP | 1 520 525 A1 | 4/2005 |
| EP | 1 621 141 A21 | 2/2006 |
| EP | 1 702 570 A1 | 9/2006 |
| EP | 1 759 640 A2 | 3/2007 |
| EP | 1 815 804 A2 | 8/2007 |
| EP | 1 825 820 | 8/2007 |
| EP | 1 929 958 | 6/2008 |
| EP | 1 994 890 A1 | 11/2008 |
| EP | 2 005 894 A2 | 12/2008 |
| EP | 2 005 895 A2 | 12/2008 |
| EP | 2 008 595 A2 | 12/2008 |
| EP | 2 090 231 | 8/2009 |
| EP | 2 090 244 | 8/2009 |
| EP | 2 198 787 A1 | 6/2010 |
| EP | 2 236 098 A2 | 10/2010 |
| EP | 2 311 386 | 4/2011 |
| JP | 2000-166933 | 6/2000 |
| JP | 2002-202213 | 7/2002 |
| JP | 07-124166 | 5/2007 |
| WO | WO 90/05489 A1 | 5/1990 |
| WO | WO 95/16221 | 6/1995 |
| WO | WO 96/22055 A1 | 7/1996 |
| WO | WO 97/01989 A1 | 1/1997 |
| WO | WO 97/13463 A1 | 4/1997 |
| WO | WO 98/17180 A1 | 4/1998 |
| WO | WO 99/02090 A1 | 1/1999 |
| WO | WO 99/45849 A1 | 9/1999 |
| WO | WO 03/082126 A1 | 10/2003 |
| WO | WO 03/088845 | 10/2003 |
| WO | WO 03/094743 | 11/2003 |
| WO | WO 03/105698 A2 | 12/2003 |
| WO | WO 2006/023578 A2 | 3/2006 |
| WO | WO 2006/044490 A2 | 4/2006 |
| WO | WO 2006/083748 A1 | 8/2006 |
| WO | WO 2007/121579 A1 | 11/2007 |
| WO | WO 2008/057281 A2 | 5/2008 |
| WO | WO 2008/109125 A1 | 9/2008 |
| WO | WO 2010/075298 A2 | 7/2010 |
| WO | WO 2011/143183 A2 | 11/2011 |
| WO | WO 2012/044848 A1 | 4/2012 |

OTHER PUBLICATIONS

International Search Report corresponding to European Application No. EP 06 01 6962.0, completed on Jan. 3, 2007 and mailed on Jan. 11, 2007; 10 pages.

International Search Report corresponding to International Application No. PCT/US05/36740, completed on Feb. 20, 2007 and mailed on Mar. 23, 2007; 8 pages.

International Search Report corresponding to International Application No. PCT/US2008/002981, completed on Jun. 9, 2008 and mailed on Jun. 26, 2008; 2 pages.

International Search Report corresponding to European Application No. EP 08 25 1779, completed on Jul. 14, 2008 and mailed on Jul. 23, 2008; 5 pages.

International Search Report corresponding to European Application No. EP 08 25 1989.3, completed on Mar. 11, 2010 and mailed on Mar. 24, 2010; 3 pages.

International Search Report corresponding to European Application No. EP 05 80 4382.9, completed on Oct. 5, 2010 and mailed on Oct. 12, 2010; 3 pages.

International Search Report corresponding to European Application No. EP 10 25 1437.9, completed on Nov. 22, 2010 and mailed on Dec. 16, 2010; 3 pages.

(56) References Cited

OTHER PUBLICATIONS

International Search Report corresponding to European Application No. EP 09 25 2897.5, completed on Feb. 7, 2011 and mailed on Feb. 15, 2011; 3 pages.
European Search Report for EP 09252794.4-1269 date of completion is Mar. 25, 2010 (3 pages).
International Search Report corresponding to European Application No. EP 10 25 0715.9, completed on Jun. 30, 2010 and mailed on Jul. 20, 2010; 3 pages.
International Search Report corresponding to European Application No. EP 10 25 0642.5, completed on Mar. 25, 2011 and mailed on Apr. 4, 2011; 4 pages.
International Search Report corresponding to European Application No. EP 12 15 0511.9, completed on Apr. 16, 2012 and mailed on Apr. 24, 2012; 7 pages.
International Search Report corresponding to European Application No. EP 12 15 2541.4, completed on Apr. 23, 2012 and mailed on May 3, 2012; 10 pages.
International Search Report corresponding to European Application No. EP 12 16 5609.4, completed on Jul. 5, 2012 and mailed on Jul. 13, 2012; 8 pages.
International Search Report corresponding to European Application No. EP 12 15 8861.0, completed on Jul. 17, 2012 and mailed on Jul. 24, 2012; 9 pages.
International Search Report corresponding to European Application No. EP 12 16 5878.5, completed on Jul. 24, 2012 and mailed on Aug. 6, 2012; 8 pages.
International Search Report corresponding to European Application No. EP 11 18 8309.6, completed on Dec. 15, 2011 and mailed on Jan. 12, 2012; 3 pages.
European Search Report for EP 12152229.6-1269 date of completion is Feb. 23, 2012 (4 pages).
Extended European Search Report corresponding to EP 12 19 6904.2, completed Mar. 28, 2013 and mailed Jul. 26, 2013; 8 pages.
Extended European Search Report corresponding to EP 12 19 8749.9, completed May 21, 2013 and mailed May 31, 2013; 8 pages.
Extended European Search Report corresponding to EP 07 00 5842.5, completed May 13, 2013 and mailed May 29, 2013; 7 pages.
Extended European Search Report corresponding to EP 12 19 8776.2, completed May 16, 2013 and mailed May 27, 2013; 8 pages.
Extended European Search Report corresponding to EP 13 15 6297.7, completed Jun. 4, 2013 and mailed Jun. 13, 2013; 7 pages.
Extended European Search Report corresponding to EP 13 17 3985.6, completed Aug. 19, 2013 and mailed Aug. 28, 2013; 6 pages.
Extended European Search Report corresponding to EP 13 17 3986.4, completed Aug. 20, 2013 and mailed Aug. 29, 2013; 7 pages.
Extended European Search Report corresponding to EP No. 12 19 1035.0, completed Jan. 11, 2013 and mailed Jan. 18, 2013; 7 pages.
Extended European Search Report corresponding to EP No. 12 18 6175.1, completed Jan. 15, 2013 and mailed Jan. 23, 2013; 7 pages.
Extended European Search Report corresponding to EP No. 12 19 1114.3, completed Jan. 23, 2013 and mailed Jan. 31, 2013; 10 pages.
Extended European Search Report corresponding to EP No. 12 19 2224.9, completed Mar. 14, 2013 and mailed Mar. 26, 2013; 8 pages.
Extended European Search Report corresponding to EP No. 12 19 6911.7, completed Apr. 18, 2013 and mailed Apr. 24, 2013; 8 pages.

* cited by examiner

SURGICAL APPARATUS INCLUDING SURGICAL BUTTRESS

CROSS-REFERENCE TO RELATED APPLICATIONS

The present application is a continuation of U.S. application Ser. No. 12/620,044 filed on Nov. 17, 2009, which is a continuation application of U.S. application Ser. No. 12/335,762, filed on Dec. 16, 2008, the entire contents of which are hereby incorporated by reference herein.

BACKGROUND

1. Technical Field

This application relates to a surgical apparatus, and more particularly, to a surgical buttress for use with a surgical stapling apparatus during operation of the stapling apparatus to apply a plurality of surgical fasteners to body tissue.

2. Background of Related Art

As medical and hospital costs continue to increase, surgeons are constantly striving to develop advanced surgical techniques. Advances in the surgical field are often related to the development of operative techniques which involve less invasive surgical procedures and reduce overall patient trauma. In this manner, the length of hospital stays can be significantly reduced, and, therefore, the hospital and medical costs can be reduced as well.

Although the present disclosure includes, but is not limited to use with endoscopic surgery, endoscopic surgery is one of the truly great advances in recent years to reduce the invasiveness of surgical procedures. Generally, endoscopic surgery involves incising through body walls for example, viewing and/or operating on the ovaries, uterus, gall bladder, bowels, kidneys, appendix, etc. There are many common endoscopic surgical procedures, including arthroscopy, laparoscopy (pelviscopy), gastroentroscopy and laryngobronchoscopy, just to name a few. Typically, trocars are utilized for creating the incisions through which the endoscopic surgery is performed. Trocar tubes or cannula devices are extended into and left in place in the abdominal wall to provide access for endoscopic surgical tools. A camera or endoscope is inserted through a relatively large diameter trocar tube which is generally located at the naval incision, and permits the visual inspection and magnification of the body cavity. The surgeon can then perform diagnostic and therapeutic procedures at the surgical site with the aid of specialized instrumentation, such as, forceps, cutters, applicators, and the like which are designed to fit through additional cannulas. Thus, instead of a large incision (typically 12 inches or larger) that cuts through major muscles, patients undergoing endoscopic surgery receive more cosmetically appealing incisions, between 5 and 10 millimeters in size. Recovery is, therefore, much quicker and patients require less anesthesia than traditional surgery. In addition, because the surgical field is greatly magnified, surgeons are better able to dissect blood vessels and control blood loss. Heat and water loss are greatly reduced as a result of the smaller incisions. In order to address the specific needs of endoscopic and/or laparoscopic surgical procedures, endoscopic surgical stapling devices have been developed and are disclosed in, for example, U.S. Pat. Nos. 5,040,715 (Green, et al.); 5,307,976 (Olson, et al.); 5,312,023 (Green, et al.); 5,318,221 (Green, et al.); 5,326,013 (Green, et al.); and 5,332,142 (Robinson, et al.).

In many surgical procedures, including those involved in open and endoscopic surgery, it is often necessary to staple tissue. It is especially challenging during endoscopic surgery because of the small openings through which the stapling of tissues must be accomplished. Instruments for this purpose can include two elongated members which are respectively used to capture or clamp tissue. Surgical devices wherein tissue is first grasped or clamped between opposing jaw structure and then joined by surgical fasteners are well known in the art. Typically, one of the members carries a fastener cartridge which houses a plurality of staples arranged in at least two lateral rows while the other member has an anvil that defines a surface for forming the staple legs as the staples are driven from the staple cartridge. The fasteners are typically in the form of surgical staples but two part polymeric fasteners can also be utilized. Generally, the stapling operation is effected by cam bars or wedges that travel longitudinally through the staple cartridge, with the cam bars acting upon staple pushers to sequentially eject the staples from the staple cartridge. A knife can travel between the staple rows to longitudinally cut and/or open the stapled tissue between the rows of staples. Such instruments are disclosed, for example, in U.S. Pat. No. 3,079,606 and U.S. Pat. No. 3,490,675.

A later stapler disclosed in U.S. Pat. No. 3,499,591 applies a double row of staples on each side of the incision. This is accomplished by providing a disposable loading unit in which a cam member moves through an elongate guide path between two sets of staggered staple carrying grooves. Staple drive members are located within the grooves and are positioned in such a manner so as to be contacted by the longitudinally moving cam member to effect ejection of the staples from the staple cartridge of the disposable loading unit. U.S. Surgical, the assignee of the present application, has manufactured and marketed endoscopic stapling instruments for several years. Examples of such instruments include the Multifire ENDO GIA* 30 and Multifire ENDO GIA* 60 instruments. Other examples of such staplers are disclosed in U.S. Pat. Nos. 4,429,695 and 5,065,929.

In staplers of the general type described above, it is conventional to provide separate anvil slots at each staple forming location. This makes it necessary to maintain relatively stringent alignment between the staple holding assembly and the anvil to assure that the staples enter the anvil slots correctly for proper clinching. The importance of maintaining good alignment between the relatively movable staple holding assembly and anvil assembly may contribute to the complexity of the instrument and to the cost of manufacturing and maintaining it. It is important that every staple be formed properly since an incompletely or improperly formed staple may leave a gap in a wound closure. Currently, surgical buttress material is also used in combination with these instruments as reinforcement to staple lines to further promote proper staple formation while reducing twisting/malformation caused by misalignment or unusual tissue while minimizing reliance on strict manufacturing tolerances. These instruments have provided significant clinical benefits. Nonetheless, improvements are possible, for example, by reducing the complexity of manufacture and/or application.

SUMMARY

The present invention relates to a surgical buttress for use with a surgical stapling apparatus. The surgical stapling apparatus includes a housing, an end effector having first and second jaws and at least one surgical buttress. A plurality of fasteners are disposed in fastener slots of the first jaw, and fastener pockets are provided on the second jaw. The at least one surgical buttress has a body portion and at least one band connected to a distal end thereof for connection to the end effector. The at least one band encircles a portion of the end effector. The body portion of the at least one surgical buttress is configured and dimensioned to substantially overlie at least some of the fastener slots of the first jaw.

The at least one surgical buttress of the surgical stapling apparatus includes a resilient portion. The resilient portion extends transversely beyond at least one side edge of at least one of the first or second jaws of the end effector. The resilient portion of the surgical stapling apparatus is configured and dimensioned to remain attached to the end effector following the firing of the surgical stapling apparatus.

The surgical stapling apparatus further includes at least one second band connected to a proximal end of the at least one surgical buttress for connection to a proximal end of the end effector. The at least one second band of the surgical stapling apparatus is configured and dimensioned to remain attached to the end effector following the firing of the surgical stapling apparatus.

The surgical stapling apparatus further includes a hook feature disposed on the proximal end of at least one of the first or second jaws of the end effector. The at least one second band is configured and dimensioned to engage the hook feature.

At least the body portion of the at least one surgical buttress of the surgical stapling apparatus includes a plurality of perforations. The perforations are disposed along the perimeter of the body portion of the surgical buttress of the surgical stapling apparatus.

At least the body portion of the at least one surgical buttress of the surgical stapling apparatus can be made from degradable materials selected from the group comprising natural collagenous materials, cat gut, or synthetic resins including those derived from alkylene carbonates including trimethylene carbonate, tetramethylene carbonate; caprolactone, valerolactone, dioxanone, polyanhydrides, polyesters, polyacrylates, polymethylmethacrylates, polyurethanes, glycolic acid, lactic acid, glycolide, lactide, polyhydroxy butyrates, polyorthoester, polyhydroxy alkanoates, homopolymers thereof, and copolymers thereof.

At least the body portion of the at least one surgical buttress of the surgical stapling apparatus can be made from non-degradable materials selected from the group comprising polyolefins, including polyethylene, polydimethylsiloxane, polypropylene, copolymers of polyethylene and polypropylene, and blends of polyethylene and polypropylene; ultra high molecular weight polyethylene, polyamides; polyesters including polyethylene terephthalate; polytetrafluoroethylene; polyether-esters including polybutester; polytetramethylene ether glycol; 1,4-butanediol; polyurethanes; and combinations thereof; silk; cotton, linen, and carbon fibers.

In one aspect of the present disclosure, a surgical buttress for use with a surgical stapling apparatus including a body portion defining a length and a width is provided. The body portion has distal and proximal ends. The body portion is configured and dimensioned to substantially overlie a portion of at least one of the fastener slots of the first jaw of an end effector of the surgical stapling apparatus or the fastener pockets of the second jaw of the end effector of the surgical stapling apparatus. At least one band is connected to the distal end of the body portion. The at least one band is configured and dimensioned to encircle a portion of the end effector.

The surgical buttress further includes a resilient portion configured and dimensioned to extend transversely beyond at least one side edge of at least one of the first or second jaws of the end effector. The resilient portion of the surgical buttress is configured and dimensioned to remain attached to the end effector following the firing of the surgical stapling apparatus.

At least a portion of the body portion of the surgical buttress includes a plurality of perforations. At least a portion of the perforations of the surgical buttress are disposed along the perimeter of the body portion.

The at least one band of the surgical buttress is configured and dimensioned to remain attached to the end effector following the firing of the surgical stapling apparatus.

At least the body portion of the surgical buttress can be made from degradable materials selected from the group comprising natural collagenous materials, cat gut, or synthetic resins including those derived from alkylene carbonates including trimethylene carbonate, tetramethylene carbonate; caprolactone, valerolactone, dioxanone, polyanhydrides, polyesters, polyacrylates, polymethylmethacrylates, polyurethanes, glycolic acid, lactic acid, glycolide, lactide, polyhydroxy butyrates, polyorthoester, polyhydroxy alkanoates, homopolymers thereof, and copolymers thereof.

At least the body portion of the surgical buttress can be made from non-degradable materials selected from the group comprising polyolefins, including polyethylene, polydimethylsiloxane, polypropylene, copolymers of polyethylene and polypropylene, and blends of polyethylene and polypropylene; ultra high molecular weight polyethylene, polyamides; polyesters including polyethylene terephthalate; polytetrafluoroethylene; polyether-esters including polybutester; polytetramethylene ether glycol; 1,4-butanediol; polyurethanes; and combinations thereof; silk; cotton, linen, and carbon fibers.

According to a further aspect of the present disclosure, a surgical stapling apparatus having a housing, an end effector including first and second jaws, and at least one surgical buttress is provided. A plurality of fasteners are disposed in fastener slots of the first jaw. Fastener pockets are provided on the second jaw. The at least one surgical buttress has a body portion and at least one band connected to a distal end thereof for connection to the end effector. The at least one band encircles a portion of the end effector. The body portion of the at least one surgical buttress is configured and dimensioned to substantially overlie at least some of the fastener pockets of the second jaw.

According to yet another aspect of the present disclosure, a method of attaching a surgical buttress to a jaw of a surgical stapling apparatus is provided. The method includes the step of: providing a surgical buttress. The surgical buttress includes a body portion defining a length and a width; the body portion having distal and proximal ends, wherein the body portion is configured and dimensioned to substantially overlie a portion of at least one of the fastener slots of the first jaw of an end effector of the surgical stapling apparatus or the fastener pockets of the second jaw of the end effector of the surgical stapling apparatus; at least one band connected to the distal end of the body portion, wherein the at least one band is configured and dimensioned to remain attached to the end effector following the firing of the surgical stapling apparatus; and a resilient portion connected to the sides of the body portion. The method further includes the steps of affixing the at least one band to the distal end of at least one of the first or second jaws of the end effector; extending the resilient portion transversely beyond at least one side edge of at least one of the first or second jaws; and selectively affixing at least one second band to the proximal end of at least one of the first or second jaws of the end effector.

BRIEF DESCRIPTION OF THE DRAWINGS

The above and other aspects, features, and advantages of the present disclosure will become more apparent in light of the following detailed description when taken in conjunction with the accompanying drawings in which.

DETAILED DESCRIPTION OF EMBODIMENTS

Particular embodiments of the present disclosure will be described herein with reference to the accompanying drawings. As shown in the drawings and as described throughout the following description, and as is traditional when referring to relative positioning on an object, the term "proximal" refers to the end of the apparatus that is closer to the user and the term "distal" refers to the end of the apparatus that is further from the user. In the following description, well-known functions or constructions are not described in detail to avoid obscuring the present disclosure in unnecessary detail.

Figure 1:
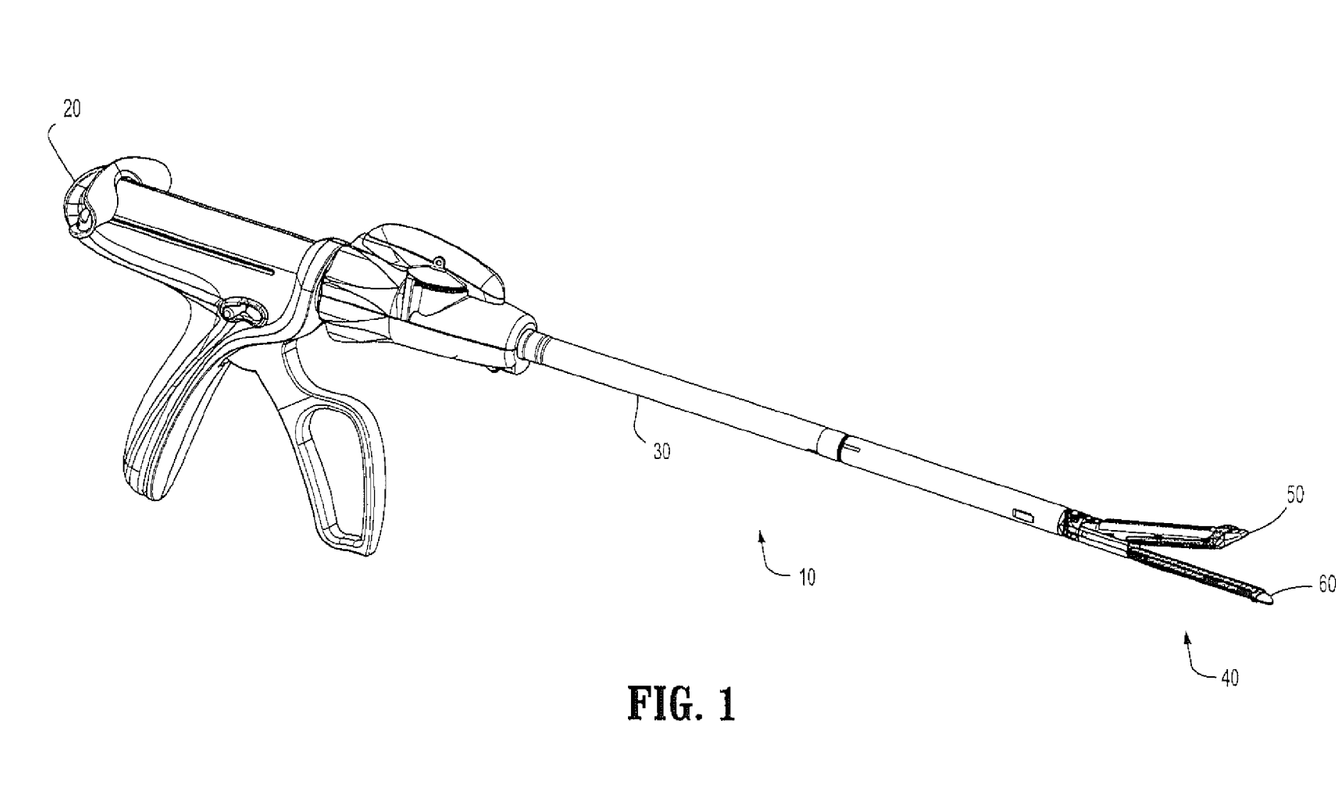
FIG. 1 is a perspective view of an endoscopic surgical stapler including a surgical buttress according to the present disclosure.
Figures 2, 2A:
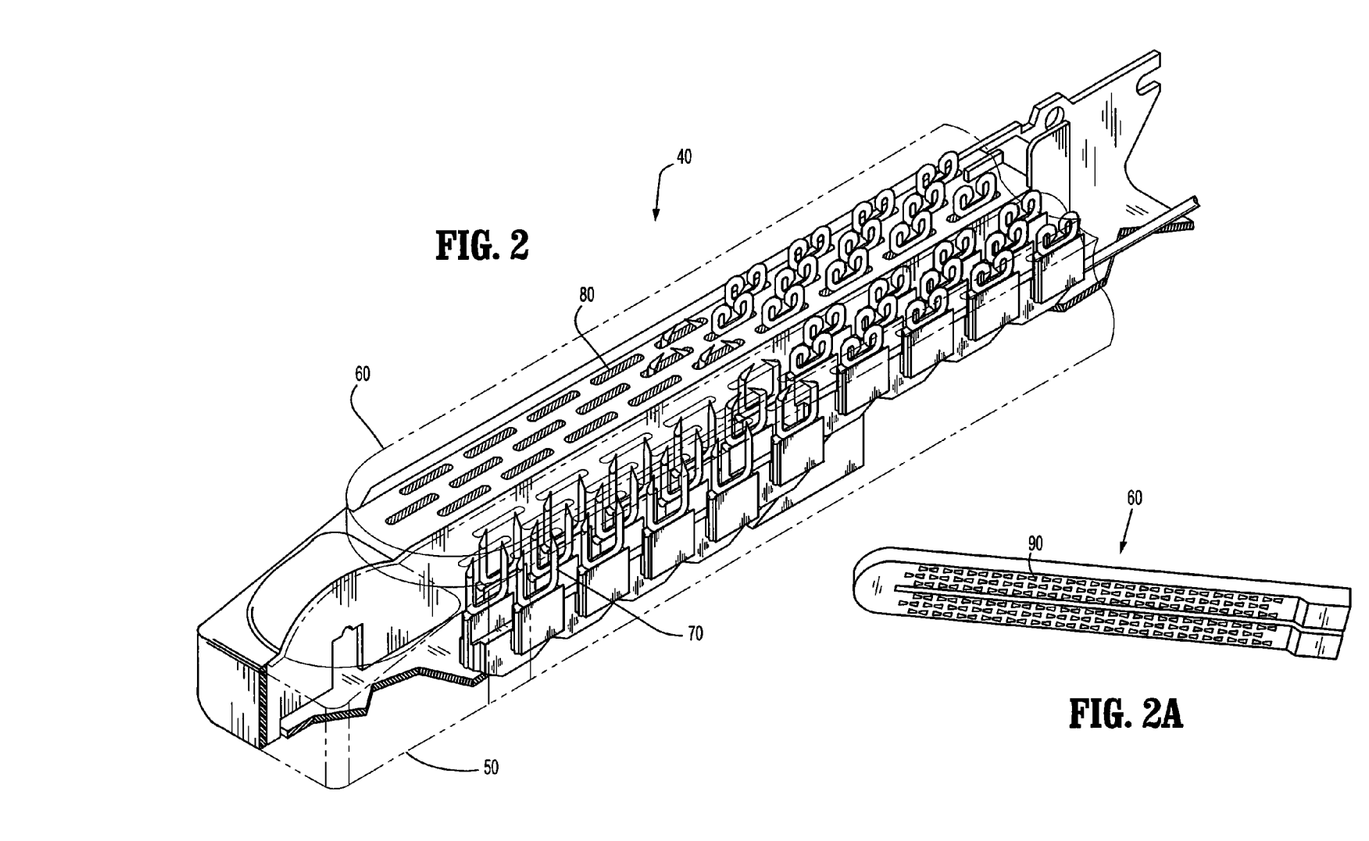
FIG. 2 is a perspective view illustrating an exemplary end effector during a fastener applying operation as fasteners are being sequentially fired.
FIG. 2A is a bottom perspective view of one embodiment of the second jaw of the exemplary end effector of FIG. 2.

Referring now to the drawings, in which like reference numerals identify identical or substantially similar parts throughout the several views, FIG. 1 illustrates a surgical stapling apparatus 10. In accordance with the present disclosure, a surgical stapling apparatus 10 includes a housing 20 and an elongate member 30 extending from the housing 20. An end effector 40 is disposed on one end of the elongate member 30. The end effector 40 includes first and second jaws 50, 60. As seen in FIGS. 2 and 2A, a plurality of fasteners 70 are disposed in fastener slots 80 and formed in fastener pockets 90. The fastener slots 80 are disposed on one of the first or second jaws 50, 60. The fastener pockets 90 are disposed on the other of the first or second jaws 50, 60.

Figure 3:
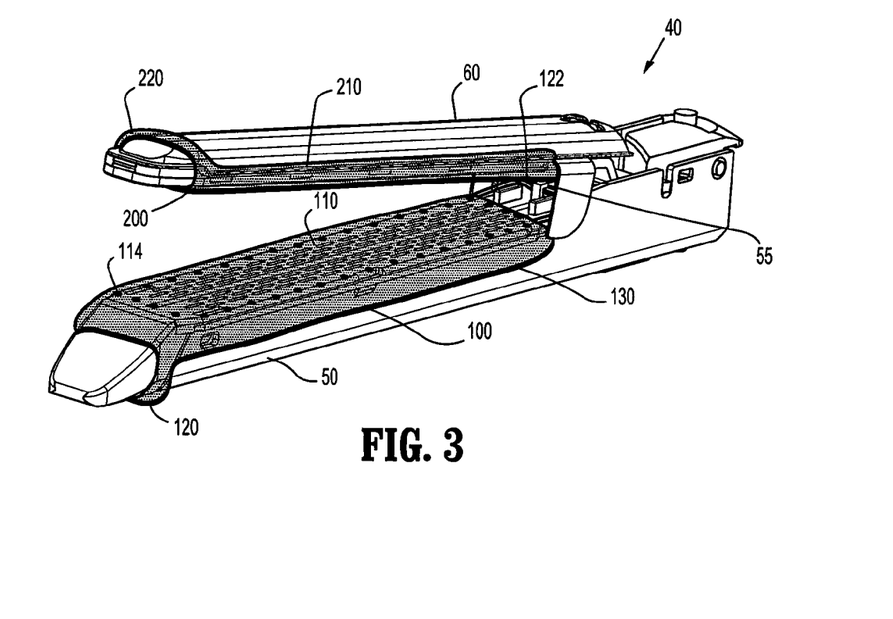
FIG. 3 is a perspective view of the end effector illustrating a surgical buttress attached to the first and second jaws thereof in accordance with the present disclosure.
Figure 4:
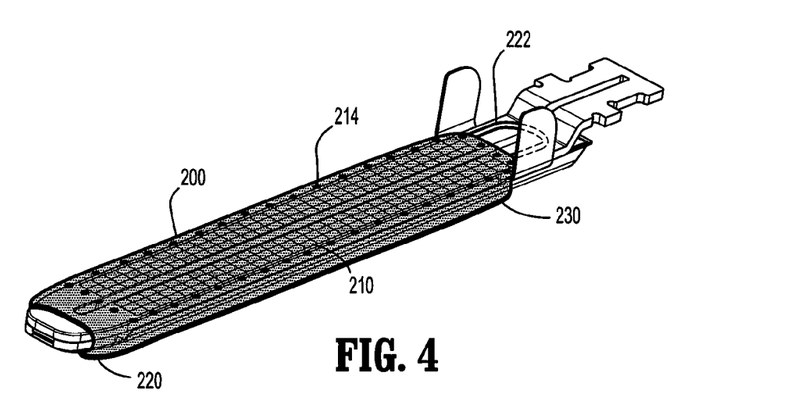
FIG. 4 is a bottom perspective view of the second jaw of FIG. 3.
Figure 5A:
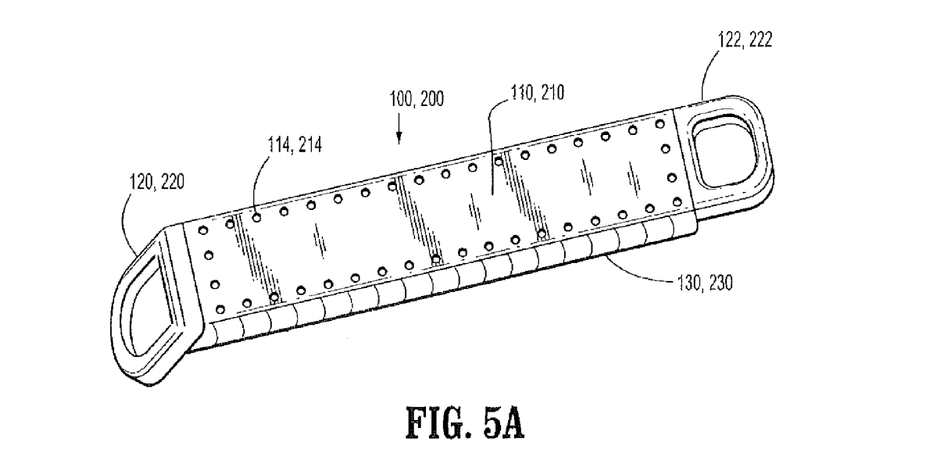
FIG. 5A is a perspective view of the surgical buttress in accordance with the present disclosure.
Figure 5B:
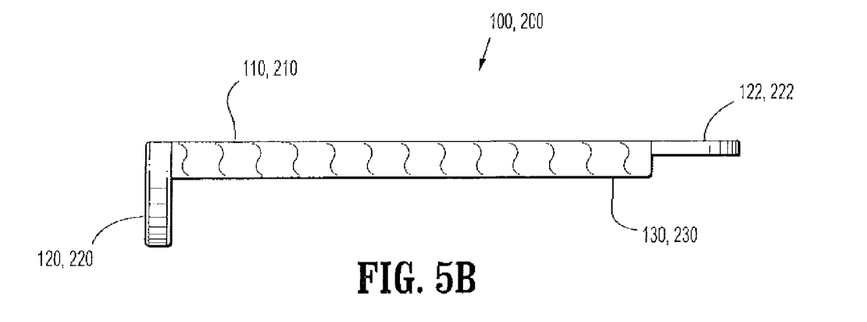
FIG. 5B is side elevational view of the surgical buttress of FIG. 5A.
Figure 5C:
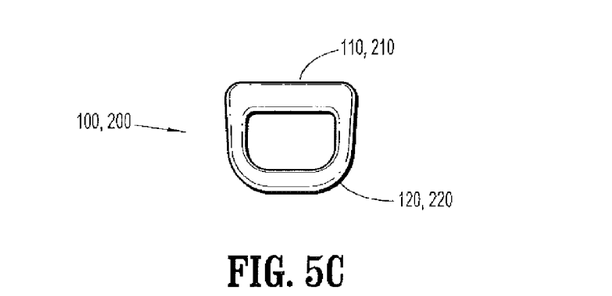
FIG. 5C is a front elevational view of the surgical buttress of FIGS. 5A and 5B.

As illustrated in FIGS. 3 and 4, a first surgical buttress 100 is shown disposed on or attached to the first jaw 50 and a second surgical buttress 200 is shown disposed on or attached to the second jaw 60. With reference to FIGS. 5A-5C, each surgical buttress 100, 200 includes a respective body portion 110, 210 having at least one distal band 120, 220 disposed at a distal end thereof for removably connecting the surgical buttress 100, 200 to a distal end of respective jaws 50, 60 of the end effector 40. Additionally, each surgical buttress 100, 200 has a proximal band 122, 222 disposed at the proximal end thereof for removably connecting the surgical buttress 100, 200 to a proximal end of respective jaws 50, 60 of the end effector 40. Each band 120, 220, 122, 222 is configured and dimensioned to encircle a portion of the end effector 40.

As used herein, the surgical buttress 100, 200 includes a pledget, gasket, buttress, or staple line reinforcement structure.

Each body portion 110, 210 defines a length and a width and is configured to substantially overlie at least a portion of the working surface of the respective first or a second jaws 50, 60 of the end effector 40 of the surgical stapling apparatus 10. Each surgical buttress 100, 200 may be configured and dimensioned to overlie at least a portion of the fastener slots 80 or the fastener pockets 90 of the respective first and second jaws 50, 60. As such, in use, the body portion 110, 210 of the surgical buttress 100, 200 provides fastener-line reinforcement for the plurality of fasteners 70 following the firing of the surgical stapling apparatus 10.

The distal bands 120, 220 are attached at the distal end of the body portions 110, 210 in such a manner so to remain attached to respective jaws 50, 60 of the end effector 40 following a firing of the stapling apparatus 10. For example, each distal band 120, 220 is configured and dimensioned to wrap around a distal end of a respective jaw 50, 60 of the end effector 40. Conversely, a proximal band 122, 222 is configured and dimensioned to wrap around a proximal end of respective jaws 50, 60. In one embodiment, as seen in FIG. 3, the proximal band 122 of the surgical buttress 100 may be configured to engage a hook feature 55 provided at the proximal end of the first jaw 50. Similarly, proximal band 222 of the surgical buttress 200 may be configured to engage the hook feature 55 provided at the proximal end of the first jaw 50.

As seen in FIG. 5C, each surgical buttress 100, 200 includes a plurality of perforations 114, 214 formed along the respective perimeter of the body portions 110, 210 thereof. In this manner, during use a central area of the body portions 110, 210 may be separated along the perforations 114, 214 following a securing thereof to tissue. It is further contemplated that perforations 114, 214 may be replaced with lines or slots of reduced thickness and may not necessarily penetrate completely through body portions 110, 210.

Referring again to FIGS. 3-4, 5A and 5C, each surgical buttress 100, 200 includes resilient side skirts 130, 230 extending transversely beyond at feast one side edge of the respective body portions 110, 210 of each surgical buttress 100, 200. It is contemplated that side skirts 130, 230 may be affixed or adhered to the sides of respective jaws 50, 60.

It is envisioned that at least body portions 110, 210 of the surgical buttress 100, 200 can be made from degradable, absorbable and/or resorbable materials. Materials such as natural collagenous materials, cat gut, or synthetic resins including those derived from alkylene carbonates including trimethylene carbonate, tetramethylene carbonate; caprolactone, valerolactone, dioxanone, polyanhydrides, polyesters, polyacrylates, polymethylmethacrylates, polyurethanes, glycolic acid, lactic acid, glycolide, lactide, polyhydroxy butyrates, polyorthoester, polyhydroxy alkanoates, homopolymers thereof, and copolymers thereof can be used.

Furthermore, it is also contemplated that at least body portions 110, 210 of the surgical buttress 100, 200 can be made from non-degradable, non-absorbable and/or non-resorbable materials. Materials such as polyolefins, including polyethylene, polydimethylsiloxane, polypropylene, copolymers of polyethylene and polypropylene, and blends of polyethylene and polypropylene; ultra high molecular weight polyethylene, polyamides; polyesters including polyethylene terephthalate; polytetrafluoroethylene; polyether-esters including polybutester; polytetramethylene ether glycol; 1,4-butanediol; polyurethanes; and combinations thereof; silk; cotton, linen, and carbon fibers can be used.

Figure 6:
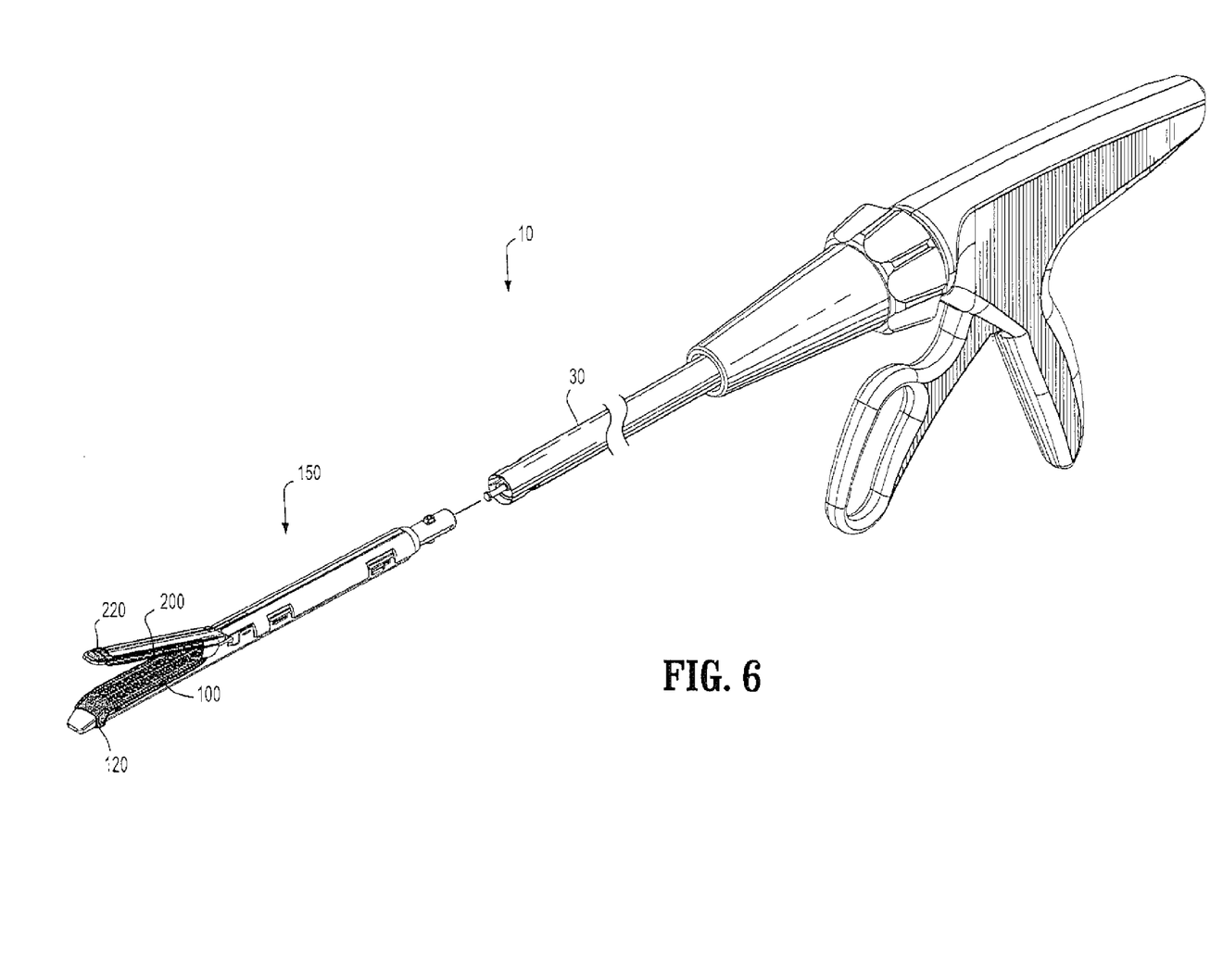
FIG. 6 is an exploded perspective view of one embodiment of a surgical stapling apparatus in accordance with the present disclosure including a single use loading unit having a surgical buttress with the single use loading unit separated from the distal end of the surgical stapling apparatus.

Referring to FIG. 6, one embodiment of the present disclosure envisions a surgical stapling apparatus 10 that includes a single use loading unit 150, which in some manifestations, is disposable. Upon firing of the surgical stapling apparatus 10, each distal band 120, 220, each proximal band 122, 222, and each resilient side skirt 130, 230 are collectively detachable from respective body portions 110, 210 when the respective first or second jaw 50, 60 is removed from the surgical site after firing of the surgical stapling apparatus 10.

A method of attaching a surgical buttress 100, 200 to a jaw 50, 60 of a surgical stapling apparatus 10 is also contemplated. According to the present disclosure, the method includes the steps of providing a surgical buttress 100, 200 in accordance with the present disclosure; affixing at least one distal band 120, 220 to the distal end of a respective jaw 50, 60 of the end effector 40; extending at least a portion of the resilient side skirts 130, 230 of the surgical buttress 100, 200 transversely beyond at least one side edge of at least one of the first or second jaws 50, 60; and selectively affixing a proximal band 122, 222 to a proximal end of the respective first or second jaw 50, 60. It is contemplated that the resilient side skirts 130, 230 may be adhered to the first or second jaws 50, 60.

During operation of a surgical stapling apparatus 10, including at least one surgical buttress 100, 200, the first and second jaws 50, 60 are clamped against tissue of a patient, and the surgical stapling apparatus 10 is fired to deploy the fasteners 70 through the fastener slots 80. Upon firing, the fasteners 70 pass through the fastener slots 80, and the legs of the fasteners 70 penetrate through a first layer of tissue, through body portions 110, 210 of the surgical buttress 100, 200, through a second layer of tissue and are formed against the fastener pockets 90, thereby affixing the body portion 110, 210 of the surgical buttress 100, 200 to the tissue. Concomitantly therewith, a knife (not shown) translatably disposed within the end effector 40 cuts through the tissue clamped between the jaws 50, 60, through at least a portion of the body portion 110, 210 of the surgical buttress 100, 200. In certain embodiments, the knife can be configured and arranged to cut through the proximal bands 122, 222, which are disposed distal of the knife prior to firing. The perforations 114, 214 disposed on the body portion 110, 210 enable a central area of the body portion 110, 210 of the surgical buttress 100, 200 to disengage or release from the end effector 40, while each distal band 120, 220, proximal band 122, 222, and the resilient side skirts 130, 230 remain attached. The central area of the body portion 110, 210 of the surgical buttresses 100, 200 remains attached to the tissue via the fasteners 70. The distal bands 120, 220 and the resilient side skirts 130, 230 remain affixed to the respective jaws 50, 60 of the end effector 40 as the end effector 40 is removed.

While using a single use loading unit 150, the user may remove the single use loading unit 150 or portions thereof from the surgical stapling apparatus 10 and subsequently dispose the single use loading unit 150 in its entirety or portions thereof. If further application is necessary, a user may replace the spent or fired single use loading unit 150 by mounting a new single use loading unit 150 onto the surgical stapling apparatus 10. The user may then repeat a fastening process.

In general, linear staplers, including open and endoscopic devices, can have two elongated members which are respectively used to capture or clamp tissue. Typically, one of the members carries a staple cartridge which houses a plurality of staples arranged in at least two lateral rows while the other member has an anvil that defines a surface for forming the staple legs as the staples are driven from the staple cartridge. Generally, the stapling operation is effected by cam bars that travel longitudinally through the staple cartridge, with the cam bars acting upon staple pushers to sequentially eject the staples from the staple cartridge. A knife can travel between the staple rows to longitudinally cut and/or open the stapled tissue between the rows of staples. Such an instrument is disclosed, for example, in U.S. Pat. No. 6,202,914, the entire content of which is incorporated herein by reference.

Some staplers apply a double row of staples on each side of the incision. This is accomplished by providing a disposable loading unit in which a cam member moves through an elongate guide path between two sets of staggered staple carrying grooves. Staple drive members are located within the grooves and are positioned in such a manner so as to be contacted by the longitudinally moving cam member to effect ejection of the staples from the staple cartridge of the disposable loading unit. An example of such a stapler is disclosed in U.S. Pat. No. 5,065,929, the entire content of which is incorporated herein by reference.

Some of the instruments described above were designed for use in conventional surgical procedures wherein surgeons have direct manual access to the operative site. However, in endoscopic or laparoscopic procedures, surgery is performed through a small incision or through a narrow cannula inserted through small entrance wounds in the skin. In order to address the specific needs of endoscopic and/or laparoscopic surgical procedures, endoscopic surgical stapling devices have been developed and are disclosed in, for example, U.S. Pat. No. 5,865,361, the entire content of which is incorporated herein by reference.

It is further contemplated that the surgical buttress may be configured for use with a circular stapling apparatus, or a semi-circular stapling apparatus. The surgical buttress includes a resilient skirt at the circumferential periphery of the stapling apparatus which is resiliently pulled over the anvil and/or tubular body portion of the stapling apparatus. The surgical buttress is retained on the stapling apparatus through the resilience of the resilient skirt and/or friction. The surgical buttress can be released from the stapling apparatus utilizing perforations around the body portion of the surgical buttress and/or through the operation of the knife of the stapling apparatus.

Surgical stapling devices for applying an annular array of staples or fasteners to tissue are well known in the art. These devices typically include means for controlling the spacing between the fastener assembly and the anvil member at the distal end of the apparatus. The fastener assembly generally includes a circular array of fasteners such as staples, anastomosis rings, and the like, while the anvil member includes means for completing the circular anastomosis, typically an array of bucket members that clinch the staples after the staples are expelled from the fastener assembly, or may include a locking member for the anastomosis ring. The means for advancing or retracting the anvil in relation to the fastener assembly typically includes a wing-nut type mechanism at a proximal end of the instrument or a rotatable knob member, both of which engage a worm gear arrangement in the handle mechanism to slowly, and methodically advance the anvil member towards the fastener assembly.

Surgical stapling devices for applying an annular array of staples, as well as devices for completing a surgical anastomosis through the provision of anastomosis rings, are well known in gastric and esophageal surgery, for example in classic or modified gastric reconstruction typically formed in an end to end, end to side, or side to side manner. In use, the instrument is positioned within the lumen of an organ such as the stomach, esophagus, or intestine in order to perform the anastomosis. The tissue is positioned between the anvil and the fastener assembly and is typically tied off, for example, by a purse string suture. Thereafter, the anvil member is advanced towards the fastener assembly by rotation of the rotatable knob or wing nut assembly at the proximal end of the instrument to hold the tissue between the anvil member and the fastener assembly. As the staples or the fasteners are expelled from the fastener assembly, a circular knife typically follows the application of the staples to excise unwanted tissue at the anastomosis site. The instrument is then removed from the lumen of the organ.

Closing mechanisms associated with these types of stapling or fastening devices typically utilize a complex worm gear arrangement or screw bearing member to open and close the spacing between the anvil and the fastener assembly. These devices generally provide a rotatable knob or wing-like assembly remote from the fastener or staple pusher member, and the worm gear mechanism is provided to translate the rotational movement of the knob into longitudinal movement of the anvil member towards the staple pusher member. In order to effect this movement, the surgeon must grasp the device with one hand while rotating the knob or wing-like assembly with the other hand. Such instruments are disclosed, for example, in U.S. Pat. No. 5,915,616, the entire content of which is incorporated herein by reference.

In another example, it is contemplated that the surgical buttress is configured for use with surgical fastening devices for simultaneously applying an array of surgical fasteners, e.g., staples or other types of fasteners that are known in the art. Such devices are used for joining body tissue such as, for example, intestinal and gastric walls with spaced parallel rows of longitudinally aligned fasteners. These surgical fastening devices reduce the time of wound closure in a surgical procedure.

Typically, these devices include a fastener holder disposed on one side of the tissue to be joined, and an anvil assembly parallel to the fastener holder on the other side of the tissue to be fastened. The fastener holder is moved linearly towards the anvil assembly so that the tissue is clamped between them. The fasteners are driven from the fastener holder so that the ends of the fasteners pass through the tissue and form finished fasteners as they make contact with the anvil assembly, thereby producing an array of finished fasteners in the tissue. The fasteners can be one or two piece and made of metal, non-absorbable polymers, or bioabsorbable polymers such as polyglycolide, polylactide, and copolymers thereof.

U.S. Pat. No. 5,137,198 to Nobis et al. ("Nobis") discloses a fastener applying device including a cartridge that is advanced towards an anvil assembly by an advancing mechanism. The advancing mechanism includes a first actuator member for advancing the cartridge towards the anvil assembly at an accelerated rate and a second actuator member spaced from the first actuator member for incrementally advancing the cartridge towards the anvil assembly.

Typically, these fastener applying devices include a pusher bar that is advanced over a predetermined stroke to interact with and eject the fasteners from the cartridge. At least one driver is positioned within the cartridge between the distal end of the pusher bar and the fasteners such that the pusher bar advances the drivers into engagement with the fasteners. The length of the drivers may be varied to facilitate ejection of different size fasteners from a fastener applying device having a fixed pusher bar stroke. Such instruments are disclosed, for example, in U.S. Pat. No. 5,964,394, the entire content of which is incorporated herein by reference.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of preferred embodiments. Thus the scope of the embodiments should be determined by the appended claims and their legal equivalents, rather than by the examples given.

What is claimed is:

1. A surgical buttress, comprising:
    an elongate body having a distal end, a proximal end, a first side edge, a second side edge, and a resilient peripheral portion which extends from at least one of the first and second side edges of the elongate body, the resilient peripheral portion configured as a resilient side skirt of the elongate body that can be resiliently pulled to engage sides of a stapler jaw; and
    a first side wall extending from the first side edge of the body, and a second side wall extending from the second side edge of the body.

2. The surgical buttress according to claim 1, further comprising:
    a first band secured to each of the first side edge and the second side edge of the body at the distal end of the body, the first band defining a first opening and being disposed at a transverse angle relative to a plane defined by the body; and
    a second band secured to each of the first side edge and the second side edge of the body at the proximal end of the body, the second band defining a second opening.

3. The surgical buttress according to claim 2, wherein the second band is disposed in the plane of the body.

4. The surgical buttress according to claim 2, wherein the first and second side walls are formed of a resilient material.

5. The surgical buttress according to claim 2, wherein at least one of the first and second openings have at least two different radii of curvature.

6. The surgical buttress according to claim 2, wherein the body includes a plurality of perforations.

7. The surgical buttress according to claim 2, wherein at least the body is made from degradable materials selected from the group comprising natural collagenous materials, cat gut, or synthetic resins including those derived from alkylene carbonates including trimethylene carbonate, tetramethylene carbonate; caprolactone, valerolactone, dioxanone, polyanhydrides, polyesters, polyacrylates, polymethylmethacrylates, polyurethanes, glycolic acid, lactic acid, glycolide, lactide, polyhydroxy butyrates, polyorthoester, polyhydroxy alkanoates, homopolymers thereof, and copolymers thereof.

8. The surgical buttress according to claim 2, wherein at least the body is made from non-degradable materials selected from the group comprising polyolefins, including polyethylene, polydimethylsiloxane, polypropylene, copolymers of polyethylene and polypropylene, and blends of polyethylene and polypropylene; ultra high molecular weight polyethylene, polyamides; polyesters including polyethylene terephthalate; polytetrafluoroethylene; polyether-esters including polybutester; polytetramethylene ether glycol; 1,4-butanediol; polyurethanes; and combinations thereof; silk; cotton, linen, and carbon fibers.

9. The surgical buttress according to claim 1, wherein the resilient peripheral portion has a resiliency, and wherein the resilient side skirt resiliently constricts the resilient peripheral portion against the stapler jaw to secure the surgical buttress to the stapler jaw.

10. A surgical buttress for use with a surgical stapling apparatus, the surgical buttress comprising:

a body having a distal end, a proximal end, a first side edge, and a second side edge, the body configured and dimensioned to substantially overlie a portion of at least one of:
   fastener slots of a first jaw of an end effector of the surgical stapling apparatus; and
   fastener pockets of a second jaw of the end effector of the surgical stapling apparatus;
a resilient peripheral wall extending from at least the first side edge of the body and the second side edge of the body, wherein the resilient peripheral wall has a resiliency;
wherein the resilient peripheral wall is configured as resilient side skirts that can be resiliently pulled to engage sides of a stapler jaw of a surgical stapling apparatus, and wherein the resilient side skirt resiliently constricts the resilient peripheral wall against the stapler jaw to secure the surgical buttress to the stapler jaw.

11. The surgical buttress according to claim 10, further comprising:
   a first resilient band secured to each of the first side edge and the second side edge of the body at the distal end of the body, the first band defining a first opening and being disposed at a transverse angle relative to a plane defined by the body; and
   a second resilient band secured to each of the first side edge and the second side edge of the body at the proximal end of the body, the second band defining a second opening.

12. The surgical buttress according to claim 11, wherein the body includes a plurality of perforations.

13. The surgical buttress according to claim 11, wherein at least one of the first and second bands defines an opening having at least two different radii of curvature.

14. The surgical buttress according to claim 11, wherein the second resilient band is disposed in the plane of the body.

15. The surgical buttress according to claim 11, wherein at least the body is made from degradable materials selected from the group comprising natural collagenous materials, cat gut, or synthetic resins including those derived from alkylene carbonates including trimethylene carbonate, tetramethylene carbonate; caprolactone, valerolactone, dioxanone, polyanhydrides, polyesters, polyacrylates, polymethylmethacrylates, polyurethanes, glycolic acid, lactic acid, glycolide, lactide, polyhydroxy butyrates, polyorthoester, polyhydroxy alkanoates, homopolymers thereof, and copolymers thereof.

16. The surgical buttress according to claim 11, wherein at least the body is made from non-degradable materials selected from the group comprising polyolefins, including polyethylene, polydimethylsiloxane, polypropylene, copolymers of polyethylene and polypropylene, and blends of polyethylene and polypropylene; ultra high molecular weight polyethylene, polyamides; polyesters including polyethylene terephthalate; polytetrafluoroethylene; polyether-esters including polybutester; polytetramethylene ether glycol; 1,4-butanediol; polyurethanes; and combinations thereof; silk; cotton, linen, and carbon fibers.

* * * * *